United States Patent
Mallo et al.

(10) Patent No.: US 10,131,729 B2
(45) Date of Patent: Nov. 20, 2018

(54) AMPHOLYTIC POLYMERS HAVING A THERMOSENSITIVE CHARACTER

(71) Applicant: SOCIETE D'EXPLOITATION DE PRODUITS POUR LES INDUSTRIES CHIMIQUES SEPPIC, Paris (FR)

(72) Inventors: Paul Mallo, Le Vesinet (FR); Olivier Braun, St Just St Rambert (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

(21) Appl. No.: 14/654,679

(22) PCT Filed: Nov. 26, 2013

(86) PCT No.: PCT/FR2013/052856
§ 371 (c)(1),
(2) Date: Jun. 22, 2015

(87) PCT Pub. No.: WO2014/096595
PCT Pub. Date: Jun. 26, 2014

(65) Prior Publication Data
US 2015/0315319 A1    Nov. 5, 2015

(30) Foreign Application Priority Data

Dec. 21, 2012 (FR) ........................ 12 62530

(51) Int. Cl.
| | |
|---|---|
| A61K 8/81 | (2006.01) |
| A61Q 19/00 | (2006.01) |
| A61Q 5/00 | (2006.01) |
| C08F 220/58 | (2006.01) |
| A61Q 5/02 | (2006.01) |
| A61Q 5/06 | (2006.01) |
| A61Q 5/12 | (2006.01) |
| A61K 8/91 | (2006.01) |
| C08F 265/10 | (2006.01) |

(52) U.S. Cl.
CPC .......... *C08F 220/58* (2013.01); *A61K 8/8158* (2013.01); *A61K 8/91* (2013.01); *A61Q 5/00* (2013.01); *A61Q 5/002* (2013.01); *A61Q 5/02* (2013.01); *A61Q 5/06* (2013.01); *A61Q 5/12* (2013.01); *A61Q 19/00* (2013.01); *C08F 265/10* (2013.01); *A61K 2800/48* (2013.01); *A61K 2800/54* (2013.01); *A61Q 5/065* (2013.01); *C08F 2220/585* (2013.01)

(58) Field of Classification Search
CPC ... C08F 20/58; C08F 265/10; C08F 2220/585
See application file for complete search history.

(56) References Cited

U.S. PATENT DOCUMENTS

| | | | |
|---|---|---|---|
| 6,830,670 B1 | 12/2004 | Viovy et al. | |
| 8,680,028 B2 | 3/2014 | Braun et al. | |
| 2002/0198328 A1* | 12/2002 | L'alloret | A61K 8/91 525/326.7 |
| 2011/0118152 A1 | 5/2011 | Braun et al. | |

FOREIGN PATENT DOCUMENTS

| | | |
|---|---|---|
| FR | 2932183 | 12/2009 |
| WO | 00-40958 | 7/2000 |
| WO | 2007-000535 | 1/2007 |

OTHER PUBLICATIONS

Salami et al., "Synthesis, Effectiveness, and Working Mechanism of Humic Acid-{sodium 2-acrylamido-2-methylpropane sulfonate-co-N,N-dimethyl acrylamide-co-acrylic acid} Graft Copolymer as High-Temperature Fluid Loss Additive in Oil Well Cementing," Journal of Applied Polymer Science, vol. 126, pp. 1449-1460 (2012).
Wu et al., "Self-assembly of a series of random copolymers bearing amphiphilic side chains," Journal of Colloid and Interface Science 349 (2010), pp. 560-564.

* cited by examiner

*Primary Examiner* — Irina S Zemel
*Assistant Examiner* — Jeffrey S Lenihan
(74) *Attorney, Agent, or Firm* — Young & Thompson

(57) ABSTRACT

A comb copolymer with a polymer backbone having grafted lateral macromonomer segments, the method of preparing, and the use thereof as a thickener in cosmetics. The polymer backbone is more than 55% and up to 90% molar ATBS, between 1% and 20% molar cationic monomer or monomer of formula (I): $CH_2=C(R_1)-C(=O)-Y-(CH_2)_m-N(R_2)(R_3)$, where m is between 1 and 4, Y is O or NH, R1 is H or $CH_2$, and $R_2$ and $R_3$ are each a methyl or ethyl radical, and optionally 0.005% to 1% molar of at least one cross-linking monomer with at least two C=C bonds. The lateral macromonomer segments are polymerized from 9% to 30% molar of N-alkyl acrylamide or N,N-dialkyl acrylamide of formula (II): $CH_2=C(R_4)-C(=O)-N(R_5)(R_6)$, where $R_4$ is H or $CH_2$ and $R_5$ and $R_6$ are H or a $C_1$ to $C_3$ alkyl radical, with at least one of $R_5$ or $R_6$ not being H.

9 Claims, No Drawings

AMPHOLYTIC POLYMERS HAVING A THERMOSENSITIVE CHARACTER

A subject matter of the present patent application is novel heat-sensitive ampholytic copolymers, the process for their preparation and their use in cosmetics.

The French patent application published under the number 2 932 183 describes novel crosslinked polyampholytes which are predominantly anionic but which also comprise cationic sites. These polyampholytes result, after swelling in aqueous fluids, in microgels which are deformable, temperature stable and mechanically stable, when they are subjected to strong shearing, and which are irreversibly adsorbed on the anionic sites of rocks. Applications are thus possible in the treatment of hydrocarbon producing wells, in particular in preventing inrushes of water.

Such crosslinked polyampholytes, which are predominantly anionic but which also comprise small proportions of cationic sites, can also advantageously be used on the skin and scalp due to their good absorption properties. However, those disclosed in this French patent application number 2 932 183 are not sufficiently adsorbed on the skin or hair to be used in cosmetics. It is the same for the heat-thickening polymers disclosed in the international application published under the number WO 00/40958.

There exists today a need for polymers having good adsorption properties and having thickening properties which are dependent on the temperature.

For this reason, according to a first aspect, a subject matter of the invention is a comb copolymer consisting of a polymer backbone to which macromonomeric side segments are grafted, characterized in that said polymer backbone consists, for 100 mol % of constituent monomer units of said comb copolymer:

of more than 55 mol %, up to 90 mol % and more particularly of 60 mol % to 80 mol % of monomer units resulting from 2-methyl 2-[(1-oxo-2-propenyl)amino]-1-propanesulfonic acid (hereinafter denoted ATBS), which is free, partially salified or completely salified;

of 1 mol % to 20 mol %, more particularly of 4 mol % to 15 mol %, either of monomeric units resulting from a cationic monomer or of monomer units resulting from a monomer of formula (I):

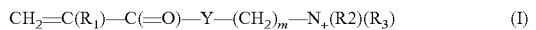

$$CH_2=C(R_1)-C(=O)-Y-(CH_2)_m-N_+(R2)(R_3) \quad (I)$$

in which m represents a number of between 1 and 4, Y represents O or NH, $R_1$ represents a hydrogen atom or a methyl radical, and $R_2$ and $R_3$, which are identical or different, represent a methyl radical or an ethyl radical;

optionally of 0.005 mol % to 1 mol %, more particularly of 0.01 mol % to 0.5 mol %, of monomer units resulting from at least one crosslinking monomer comprising at least two carbon-carbon double bonds, and in that said macromonomeric side segments result, for 100 mol % constituent of said comb copolymer, from the polymerization of 9 mol % to 30 mol % and more particularly of 15 mol % to 25 mol % of N-alkylacrylamide or N,N-dialkylacrylamide of formula (II):

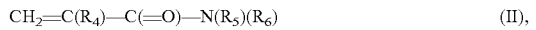

$$CH_2=C(R_4)-C(=O)-N(R_5)(R_6) \quad (II),$$

in which $R_4$ represents a hydrogen atom or a methyl radical and $R_5$ and $R_6$ represent, independently of one another, a hydrogen atom or an alkyl radical comprising from 1 to 3 carbon atoms which is optionally substituted by a hydroxyl group, it being understood that at least one of the $R_5$ or $R_6$ radicals does not represent a hydrogen atom.

The crosslinking monomers comprising at least two carbon-carbon double bonds include, for example, ethylene glycol dimethacrylate, tetraallyloxyethane, ethylene glycol diacrylate, diallylurea, triallylamine, trimethylolpropane triacrylate or methylenebis(acrylamide), or a mixture of these compounds.

According to a specific aspect of the process as defined above, in stage e) as described above, the crosslinking agent is more particularly employed in a molar proportion of greater than or equal to 0.01% and less than or equal to 0.25%.

According to two specific aspects of the present invention, said comb copolymer as defined above is characterized in that, when said polymer backbone comprises monomer units resulting from the monomer of formula (I), m is equal to 2 or to 3 in said formula (I) and/or $R_2$ and $R_3$ each represents a methyl radical.

According to these specific aspects comb copolymer as defined above is characterized in that, when said polymer backbone comprises monomer units resulting from the monomer of formula (I), these monomer units result from:
dimethylaminoethyl methacrylate (hereinafter denoted DMAEMA), or
N-[3-(dimethylamino)propyl]acrylamide (hereinafter denoted DMAPAA).

Cationic monomer denotes, for the comb copolymer as defined above, mainly a monomer comprising a quaternary ammonium functional group and less one ethylene bond. Such a monomer is generally available in the form in particular of a strong acid salt.

Strong acid salt more particularly denotes the sulfate, nitrate, sulfonate, phosphate, phosphonate or halides, such as the bromide, chloride or iodide, of said monomers having a quaternary ammonium functional group.

According to another specific aspect of the present invention, said comb copolymer as defined above is characterized in that, when said polymer backbone comprises monomer units resulting from a cationic monomer, these monomer units result from the cationic monomer of formula (III):

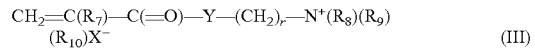

$$CH_2=C(R_7)-C(=O)-Y-(CH_2)_r-N^+(R_8)(R_9)$$
$$(R_{10})X^- \quad (III)$$

in which r represents a number of between 1 and 4, Y represents O or NH, $R_7$ represents a hydrogen atom or a methyl radical, $R_8$ and $R_9$ and $R_{10}$, which are identical or different, represent a methyl radical or an ethyl radical and the anion $X^-$ represents an anion chosen from bromide or chloride ions.

According to this other specific aspect, when said polymer backbone comprises monomer units resulting from the cationic monomer of formula (III), these monomer units result from the following quaternary ammonium salts:
the N,N,N-trimethyl-3-[(2-methyl-1-oxo-2-propenyl)amino]propanammonium salt;
the N,N,N-trimethyl-3-[(1-oxo-2-propenyl)amino]propanammonium salt;
the N,N,N-trimethyl-2-[(1-oxo-2-propenyl)oxy]ethanammonium salt; or
the N,N,N-trimethyl-2-[(2-methyl-1-oxo-2-propenyl)oxy]ethanammonium salt, and very particularly from:
N,N,N-trimethyl-3-[(1-oxo-2-propenyl)amino]propanammonium chloride (known as APTAC);
N,N,N-trimethyl-3-[(2-methyl-1-oxo-2-propenyl)amino] propanammonium chloride (known as MAPTAC);
N,N,N-trimethyl-2-[(1-oxo-2-propenyl)oxy]ethanammonium chloride (known as ADQUAT); or N,N,N-trimethyl-2-[(2-methyl-1-oxo-2-propenyl)oxy]
ethanammonium chloride (known as MADQUAT™);
and preferably from:
N,N,N-trimethyl-3-[(1-oxo-2-propenyl)amino]propan-
ammonium chloride, or
N,N,N-trimethyl-2-[(2-methyl-1-oxo-2-propenyl)oxy]
ethanammonium chloride.

According to another specific aspect of the present invention, said comb copolymer is characterized in that said macromonomeric side segments result from the polymerization of the compound of formula (II) as defined above in which $R_4$ represents a hydrogen atom or a methyl radical and $R_5$ represents a hydrogen atom and $R_6$ represents an alkyl radical comprising from 1 to 3 carbon atoms which is optionally substituted by a hydroxyl group.

According to this specific aspect, the compound of formula (II) is more particularly chosen from N-methylmethacrylamide, N-ethylmethacrylamide, N-propylmethacrylamide, N-isopropylmethacrylamide, N-(2-hydroxyethyl)methacrylamide, N-methylacrylamide, N-ethylacrylamide, N-propylacrylamide, N-isopropylacrylamide or N-(2-hydroxyethyl)acrylamide.

According to this more specific aspect of the present invention, the compound of formula (II) is N-isopropylacrylamide (hereinafter denoted NIPAM).

According to another specific aspect of the present invention, said comb copolymer is characterized in that said macromonomeric side segments result from the polymerization of the compound of formula (II) as defined above in which $R_4$ represents a hydrogen atom or a methyl radical and $R_5$ and $R_6$ each represents a methyl radical or an ethyl radical.

According to this specific aspect, the compound of formula (II) is more particularly chosen from N,N-dimethylacrylamide, N,N-diethylacrylamide, N,N-dimethylmethacrylamide or N,N-diethylmethacrylamide.

Another subject matter of the invention is a process for the preparation of the comb copolymer as defined above, comprising the following successive stages:

a stage (a) of reaction of the compound of formula (II):

$$CH_2=C(R_2)-C(=O)-N(R_3)(R_4) \quad\quad (II),$$

in which $R_2$ represents a hydrogen atom or a methyl group, $R_3$ represents a hydrogen atom or a linear or branched alkyl radical comprising from 1 to 4 carbon atoms and $R_4$, which is identical to or different from $R_3$, represents a linear or branched alkyl radical comprising from 1 to 4 carbon atoms, with a chain-limiting compound of formula (IVa):

$$HS-R_1-NH_2 \quad\quad (IVa)$$

or of formula (IVb):

$$HS-R_1-C(=O)-OH \quad\quad (IVb)$$

in which formula (IVa) or (IVb) $R_1$ represents a divalent radical comprising from 1 to 4 carbon atoms, in the presence of a polymerization initiator, in a tert-butanol/water mixture, in order to obtain a poly(N-alkylacrylamide) or poly(N,N-dialkylacrylamide) telomer of formula (Va):

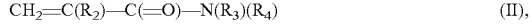

$$H_2N-R_1-S-\{CH_2-C(R)[C(=O)N(R_3)(R_4)]-\}_n-H \quad\quad (Va);$$

or of formula (Vb):

$$HO-C(=O)-R_1-S-\{CH_2-C(R_2)[C(=O)N(R_3)R_4)]-\}_n-H \quad\quad (Vb);$$

in which formula (Va) or (Vb) n represents an integer of greater than or equal to 2 and less than or equal to 100; optionally a stage (b) of isolation and/or drying of said telomer of formula (Va) or of formula (Vb) obtained in stage (a);

a stage (c) of reaction in tert-butanol of the telomer of formula (Va) or of formula (Vb) obtained in stage (a), or optionally in stage (b), with glycidyl methacrylate (VI) and in a (VI)/(IVa) or (VI)/(IVb) molar ratio of less than or equal to 10 and greater than or equal to 1, while maintaining the pH of the reaction medium at a value of greater than 10 and less than or equal to 13, more particularly of greater than or equal to 11 and less than or equal to 12, in order to obtain, after adjustment of the pH to a value of greater than or equal to 7 and less than or equal to 9, preferably less than or equal to 8, a solution of the macromonomer of formula (VIIa):

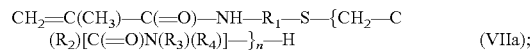

$$CH_2=C(CH_3)-C(=O)-NH-R_1-S-\{CH_2-C(R_2)[C(=O)N(R_3)(R_4)]-\}_n-H \quad\quad (VIIa);$$

or of formula (VIIb):

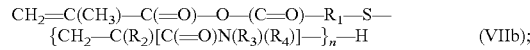

$$CH_2=C(CH_3)-C(=O)-O-(C=O)-R_1-S-\{CH_2-C(R_2)[C(=O)N(R_3)(R_4)]-\}_n-H \quad\quad (VIIb);$$

optionally a stage (d) of isolation and/or drying of said macromonomer of formula (VIIa) or of formula (VIIb) obtained in stage (c);

a stage (e) of copolymerization in tert-butanol of said macromonomer of formula (VIIa) or of formula (VIIb) resulting from stage (c) or from stage (d) with 2-acrylamido-2-methylpropanesulfonic acid and either the cationic monomer or the monomer of formula (I) as defined above and/or the crosslinking monomer or monomers comprising at least two carbon-carbon double bonds in the desired molar proportions, and, if desired, a stage (f) of purification of the comb copolymer obtained in stage (e).

tert-Butanol/water mixture denotes, in the process as defined above, a mixture having a proportion by volume of water of less than or equal to 50%.

By virtue of its cationic nature and its heat-thickening properties, the polyelectrolyte which is a subject matter of the present invention is advantageously used as thickener and/or as emulsifier in cosmetic or pharmaceutical compositions intended for caring for and/or conditioning the hair.

For this reason, according to another aspect, a subject matter of the invention is the use of the comb copolymer as defined above as thickening agent in cosmetic or pharmaceutical compositions and more particularly in those intended for caring for and/or conditioning the hair.

The polyelectrolyte which is a subject matter of the present invention can be formulated in cosmetic or pharmaceutical formulations such as foams, gels, lotions, sprays, shampoos, conditioners, hand and body lotions, sunscreens and more generally care products.

In the case of the treatment or maintenance of the hair, such cosmetic or pharmaceutical compositions are normally provided in the form of shampoos, emulsions, microemulsions and, in particular in the case of conditioners, sprayable emulsions.

According to a final aspect, a subject matter of the invention is a cosmetic or pharmaceutical composition, characterized in that it comprises, as thickening agent, an effective amount of the comb copolymer as defined above.

Effective amount is understood to mean a proportion by weight of between approximately 0.1% and approximately 5% by weight of the polyelectrolyte as defined above.

The following examples illustrate the present invention without, however, limiting it.

The following example illustrates the invention without, however, limiting it.

Example 1 of Synthesis of the ATBS(NH$_4$)/DMAPAM/NIPAM Copolymer Molar Ratio: 70.6/7.8/21.6

(1) Preparation of a Poly(N-Isopropylacrylamide) Telomer 60 g of N-isopropylacrylamide (NIPAM) are dissolved at 25° C. in 75 g of a tert-butanol/water (50/50 by volume) mixture in a thermostatically controlled reactor, which is stirred for approximately 1 hour while flushing with nitrogen. 0.9 g of 2-aminoethanethiol hydrochloride (AET.HCl) is subsequently added. The polymerization is initiated by adding 1.33 g of dilauroyl peroxide, the temperature being brought to 60° C., and then the reaction mixture is left stirring for a further three and a half hours while flushing with nitrogen. 87 g of tert-butanol are subsequently added to result in a white and pasty final reaction mixture.

(2) Preparation of the Macromonomer 0.5 g of a 48% by weight solution of sodium hydroxide in tert-butanol is added to the reaction medium obtained in stage (1) maintained at a temperature of 10° C., in order to bring the pH to approximately 12 during. 3.16 g of glycidyl methacrylate are then added and the reaction is left to take place for one hour. At the end of the reaction, approximately 1.3 g of 15% hydrochloric acid in water are added in order to lower the pH to a value of between 7 and 8.

The solution obtained comprises 28.1% by weight of NIPAM macromonomer and 17% by weight of water.

(3) Synthesis of the Comb Copolymer 40.5 g of the solution obtained in stage 2 are diluted in 487.5 g of tert-butanol in the reactor thermostatically controlled at 25° C.; 67.7 g of 2-acrylamido-2-methylpropanesulfonic acid powder and 5.7 g of N-[3-(dimethylamino)propyl]acrylamide (DMAPAM) are added thereto; 4.95 g of ammonia are injected into the reaction mixture, so as to obtain a pH approximately equal to 6. 0.5 g of water and 0.48 g of trimethylolpropane triacrylate (TMPTA) are then added. After sparging with nitrogen for 1 h and heating to 60° C., the polymerization is initiated with 1 g of dilauroyl peroxide. After reacting for 3 h, the product is emptied, filtered and dried. The desired comb copolymer is obtained in the form of a white powder [referred to in the following examples as copolymer (1)].

Viscosity of a 1% solution of the comb copolymer in water at 25° C.:
μ=10 000 mPa·s (Brookfield RVT Spindle 4; Rate: 5 revolutions/minute)
Viscosity of a 1% solution of the comb copolymer in water at 50° C.:
μ=50 000 mPa·s (Brookfield RVT Spindle 5; Rate: 5 revolutions/minute)
This difference in viscosity observed between 25° C. and 50° C. is characteristic of a heat-sensitive polymer.

Example 2: Antistress Hair Care Product

| Formula | |
|---|---|
| Phase A | |
| Water: | q.s. for 100% |
| Xanthan gum | 0.50% |
| Phase B | |
| Sepicap ™ MP: | 3.00% |
| Phase C | |
| Copolymer 1: | 4.00% |
| Phase D | |
| Butylene glycol: | 5.00% |
| Lanol ™ 99: | 5.00% |
| Sepicide ™ HB: | 0.30% |
| Sepicide ™ CI: | 0.20% |
| Fragrance | 0.20% |

Procedure

The xanthan gum is dispersed in the water with a deflocculator. Sepicap ™ MP is subsequently added, followed by the compound 1; it is dispersed and then the ingredients of phase D are added.

Example 3: Restructuring Cream Mask for Stressed and Embrittled Hair

| Formula | |
|---|---|
| Phase A | |
| Montanov ™ 82: | 3.00% |
| Lanol ™ P: | 6.00% |
| Amonyl ™ DM: | 1.00% |
| Isostearyl isononanoate: | 5.00% |
| Copolymer 1: | 2.50% |
| Phase B | |
| Water: | q.s. for 100% |
| Phase C | |
| Sepicap ™ MP: | 3.00% |
| Sepicide ™ HB: | 0.30% |
| Sepicide ™ CI: | 0.20% |

Procedure

Phase A is melted at 75° C. Phase B is heated to 75° C. A is emulsified in B. The constituents of phase C are introduced at approximately 40° C.

Example 4: Purifying Facial Gel

| Formula | |
|---|---|
| Phase A | |
| Montaline ™ C 40: | 7.00% |
| Pearlescent base 2078: | 5.00% |
| Copolymer 1: | 2.00% |
| Phase B | |
| Water: | q.s. for 100% |

Example 5: Dye Shampoo

| Formula | |
|---|---|
| Phase A | |
| Montaline ™ C 40: | 15.00% |
| Disodium cocoamphoacetate: | 5.00% |
| Cetrimonium chloride: | 1.00% |
| Sepiperl ™ N: | 3.00% |
| Copolymer 1: | 3.00% |
| Phase B | |
| Color | q.s. |
| Water | q.s. for 100% |

Example 6: Fluid Emulsion at Alkaline pH

| | |
|---|---|
| Marcol ™ 82: | 5.0% |
| Sodium hydroxide: | 10.0% |
| Water: | q.s. for 100% |
| Copolymer 1: | 1.5% |

Example 7: Rinse-Off Restructuring Cream Mask for Stressed and Embrittled Hair

| | |
|---|---|
| Ketrol ™ T: | 0.5% |
| Pecosil ™ SPP50: | 0.75% |
| N-Cocoyl amino acids: | 0.70% |
| Butylene glycol: | 3.0% |
| Copolymer 1: | 3.0% |
| Montanov ™ 82: | 3.0% |
| Jojoba oil: | 1.0% |
| Lanol ™ P: | 6.0% |
| Amonyl ™ DM: | 1.0% |
| Lanol ™ 99: | 5.0% |
| Sepicide ™ HB: | 0.3% |
| Sepicide ™ CI: | 0.2% |
| Fragrance: | 0.2% |
| Water: | q.s. for 100% |

Example 8: Hair Lotion

| | |
|---|---|
| Butylene glycol: | 3.0% |
| Copolymer 1: | 3.0% |
| Simulsol ™ 1293: | 3.0% |
| Lactic acid: | q.s. pH = 6 |
| Sepicide ™ HB: | 0.2% |
| Sepicide ™ CI: | 0.3% |
| Fragrance: | 0.3% |
| Water: | q.s. for 100% |

Example 9: Protective and Relaxing Shampoo

| | |
|---|---|
| Amonyl ™ 675 SB: | 5.0% |
| 28% Sodium lauryl ether sulfate: | 35.0% |
| Copolymer 1: | 3.0% |
| Sepicide ™ HB: | 0.5% |
| Sepicide ™ CI: | 0.3% |
| Sodium hydroxide: | q.s. pH = 7.2 |
| Fragrance: | 0.3% |
| Dye (FDC Blue 1/Yellow 5): | q.s. |
| Water: | q.s. for 100% |

Example 10: Leave-on Protector; Antistress Hair Care Product

| | |
|---|---|
| Ketrol ™ T: | 0.5% |
| Mixture of cocoyl amino acids: | 3.0% |
| Butylene glycol: | 5.0% |
| DC 1501: | 5.0% |
| Copolymer 1: | 4.0% |
| Sepicide ™ HB: | 0.5% |
| Sepicide ™ CI: | 0.3% |
| Fragrance: | 0.3% |
| Water: | q.s. for 100% |

The definitions of the commercial products used in the examples are as follows:
Montaline™ C40: (cocammoniumcarbamoyl chloride), sold by Seppic.
Sepiperl™ N: (cocoyl glucoside 1 cocoyl alcohol), sold by Seppic.
Amonylt™ DM: (Quaternium 82), sold by Seppic.
Sepicap™ MP: (Sodium cocoyl amino acids 1 potassium dimethicone copolyol panthenyl phosphate), sold by Seppic.
Simulsol™ 1293 is hydrogenated and ethoxylated castor oil, with an ethoxylation number equal to 40, sold by Seppic.
Ketrol™ T is xanthan gum, sold by Kelco.
Lanol™ 99 is isononyl isononanoate, sold by Seppic.
DC1501 is a mixture of cyclopentasiloxane and dimethiconol, sold by Dow Chemical.
Montanov™ 82 is an emulsifying agent based on cetearyl alcohol and on cocoyl glucoside.
Sepicide™ Cl, imidazolidinyl urea, is a preservative, sold by Seppic.
Sepicide™ HB, which is a mixture of phenoxyethanol, methylparaben, ethylparaben, propylparaben and butylparaben, is a preservative, sold by Seppic.
Lanol™ P is an additive having a stabilizing effect, sold by Seppic.

The invention claimed is:
1. A comb copolymer consisting of a polymer backbone to which macromonomeric side segments are grafted, wherein said polymer backbone consists, for 100 mol % of constituent monomer units of said comb copolymer:
of more than 55 mol %, up to 90 mol % of monomer units resulting from 2-methyl 2-[(1-oxo-2-propenyl)amino]-1-propanesulfonic acid (hereinafter denoted ATBS), which is free, partially salified or completely salified;
of 1 mol % to 20 mol % of monomeric units resulting from a monomer of dimethylaminoethyl methacrylate or N-[3-(dimethylamino)propyl]acrylamide;
optionally of 0.005 mol % to 1 mol % of monomer units resulting from at least one crosslinking monomer comprising at least two carbon-carbon double bonds,
and said macromonomeric side segments result, for 100 mol % constituent of said comb copolymer, from the polymerization of 9 mol % to 30 mol % of an N-alkylacrylamide selected from the group consisting of N-methylmethacrylamide, N-ethylmethacrylamide, N-propylmethacrylamide, N-isopropylmethacrylamide, N-(2-hydroxyethyl)methacrylamide, N-methylacrylamide, N-ethylacrylamide, N-propylacrylamide, N-isopropylacrylamide, and N-(2-hydroxyethyl)acrylamide.

2. The comb copolymer as defined in claim 1, wherein the N-alkylacrylamide is N-isopropylacrylamide.

3. The comb copolymer as defined in claim 1, wherein the monomer units resulting from 2-methyl 2-[(1-oxo-2-propenyl)amino]-1-propanesulfonic acid (hereinafter denoted ATBS) are 60 mol % to 80 mol % of the comb copolymer.

4. The comb copolymer as defined in claim 1, wherein the monomeric units resulting from a monomer of dimethylaminoethyl methacrylate or N-[3-(dimethylamino)propyl]acrylamide are 4 mol % to 15 mol % of the comb copolymer.

5. The comb copolymer as defined in claim 1, wherein the monomer units resulting from at least one crosslinking monomer comprising at least two carbon-carbon double bonds are 0.01 mol % to 0.5 mol % of the comb copolymer.

6. The comb copolymer as defined in claim 1, wherein the macromonomeric side segments result from the polymerization of 15 mol % to 25 mol % of said N-alkylacrylamide.

7. A process for preparing the comb copolymer as defined in claim 1, comprising the steps of:
(a) reacting:
an N-alkylacrylamide compound selected from the group consisting of N-methylmethacrylamide, N-ethylmethacrylamide, N-propylmethacrylamide, N-isopropylmethacrylamide, N-(2-hydroxyethyl)methacrylamide, N-methylacrylamide, N-ethylacrylamide, N-propylacrylamide, N-isopropylacrylamide, and N-(2-hydroxyethyl)acrylamide, said N-alkylacrylamide compound being defined according to formula (II):

$$CH_2=C(R_2)-C(=O)-N(R_3)(R_4) \quad (II),$$

in which, depending on said N-alkylacrylamide compound, $R_2$ represents a hydrogen atom or a methyl group, $R_3$ represents a hydrogen atom and $R_4$ represents a linear or branched alkyl radical comprising from 1 to 3 carbon atoms, optionally substituted by a hydroxyl group,
with
a chain-limiting compound of formula (IVa):

$$HS-R_1-NH_2 \quad (IVa)$$

or of formula (IVb):

$$HS-R_1-C(=O)-OH \quad (IVb)$$

in which formula (IVa) or (IVb) $R_1$ represents a divalent radical comprising from 1 to 4 carbon atoms, in the presence of a polymerization initiator, in a tert-butanol/water mixture, in order to obtain a poly(N-alkylacrylamide) telomer of formula (Va):

$$H_2N-R_1-S-\{CH_2-C(R_2)[C(=O)N(R_3)(R_4)]-\}_n-H \quad (Va)$$

or of formula (Vb):

$$HO-C(=O)-R_1-S-\{CH_2-C(R_2)[C(=O)N(R_3)(R_4)]-\}_n-H \quad (Vb),$$

in which formula (Va) or (Vb) n represents an integer of greater than or equal to 2 and less than or equal to 100;
optionally (b) isolating and/or drying of said telomer of formula (Va) or of formula (Vb) obtained in step (a);
(c) reacting in tert-butanol of the telomer of formula (Va) or of formula (Vb) obtained in step (a), or optionally in step (b), with glycidyl methacrylate (VI) and in a (VI)/(IVa) or (VI)/(IVb) molar ratio of less than or equal to 10 and greater than or equal to 1, while maintaining the pH of the reaction medium at a value of greater than 10 and less than or equal to 13 in order to obtain, after adjustment of the pH to a value of greater than or equal to 7 and less than or equal to 9 a solution of the macromonomer of formula (VIIa):

$$CH_2=C(CH_3)-C(=O)-NH-R_1-S-\{CH_2-C(R_2)[C(=O)N(R_3)(R_4)]-\}_n-H \quad (VIIa);$$

or of formula (VIIb):

$$CH_2=C(CH_3)-C(=O)-O-(C=O)-R_1-S-\{CH_2-C(R_2)[C(=O)N(R_3)(R_4)]-\}_n-H \quad (VIIb);$$

optionally (d) isolating and/or drying of said macromonomer of formula (VIIa) or of formula (VIIb) obtained in step (c);
(e) copolymerizing in tert-butanol of said macromonomer of formula (VIIa) or of formula (VIIb) resulting from step (c) or from optional step (d) with 2-acrylamido-2-methylpropanesulfonic acid and dimethylaminoethyl methacrylate or N-[3-(dimethylamino)propyl]acrylamide, and optionally with at least one crosslinking monomer comprising at least two carbon-carbon double bonds in the desired molar proportions, and,
optionally (f) purifying the comb copolymer obtained in step (e).

8. A method for caring for and/or conditioning the hair, comprising applying an effective amount of a cosmetic or pharmaceutical composition comprising the comb copolymer as defined in claim 1.

9. A cosmetic or pharmaceutical composition, comprising, as thickening agent, an effective amount of the comb copolymer as defined in claim 1.

\* \* \* \* \*